United States Patent
Raman et al.

(10) Patent No.: US 7,052,709 B1
(45) Date of Patent: May 30, 2006

(54) SUBSTANCE DELIVERY DEVICE (75) Inventors: Aroon Raman, Mysore (IN); Krishna Swamy Raja, Mysore (IN); Benoy Rema, Mysore (IN); Gubbi Krishnappa Natesh, Mysore (IN); Satheesh Kumar, Karnataka (IN); Shankar Manjunatha, Karnataka (IN)

(73) Assignee: Raman Boards Limited (IN)

( * ) Notice: Subject to any disclaimer, the term of this patent is extended or adjusted under 35 U.S.C. 154(b) by 0 days.

(21) Appl. No.: 10/019,634

(22) PCT Filed: Jun. 29, 2000

(86) PCT No.: PCT/IB00/00883

§ 371 (c)(1),
(2), (4) Date: Dec. 27, 2001

(87) PCT Pub. No.: WO01/00105

PCT Pub. Date: Jan. 4, 2001

(30) Foreign Application Priority Data

Jun. 29, 1999 (GB) ................................. 9915085.6

(51) Int. Cl.
*A01N 25/20* (2006.01)

(52) U.S. Cl. .................... 424/411; 43/124; 43/127; 43/144; 424/40; 424/400; 424/405; 424/406; 424/409; 424/416; 424/DIG. 10; 424/725; 424/195.18; 424/739; 424/750; 424/778; 514/65; 514/521; 514/531; 514/703; 514/739; 514/919

(58) Field of Classification Search ............... 424/405, 424/409, 411, 421, 40, 125, 709, 195.18, 424/DIG. 10, 406, 750, 739; 43/124, 125, 43/127, 144; 514/919, 65, 521, 531, 703, 514/739
See application file for complete search history.

(56) References Cited

U.S. PATENT DOCUMENTS

| | | | | |
|---|---|---|---|---|
| 2,224,622 A | * | 12/1940 | Waples | ........................ 167/49 |
| 3,257,267 A | * | 6/1966 | Hay | ............................ 162/159 |
| 3,767,785 A | * | 10/1973 | Bordenca | ..................... 424/29 |
| 3,785,561 A | * | 1/1974 | Confino et al. | ............... 239/60 |

(Continued)

FOREIGN PATENT DOCUMENTS

| | | |
|---|---|---|
| CN | 2057055 U | 5/1990 |
| CN | 1076828 A | 10/1993 |
| CN | 2226819 Y | 5/1996 |
| CN | 1173968 A | 2/1998 |

(Continued)

OTHER PUBLICATIONS

Translation of Abstracts for Documents A3-A8.

*Primary Examiner*—Neil S. Levy
(74) *Attorney, Agent, or Firm*—Daniel B. Schein, Esq.

(57) ABSTRACT

A substance delivery device includes a combustible paperboard strip and at least one substance toxic to insects and a perfume. The delivery device can take the form of a coil and includes a flexible backing sheet for supporting the combustible paperboard strip. The flexible backing sheet is not capable of combustion. Additionally, the material of the paperboard strip can include a combustion promoter.

31 Claims, 5 Drawing Sheets

U.S. PATENT DOCUMENTS

| | | | |
|---|---|---|---|
| 4,005,718 A | * | 2/1977 | Prouse et al. ............... 131/369 |
| 4,144,318 A | * | 3/1979 | D'Orazio ..................... 424/40 |
| 4,515,808 A | * | 5/1985 | Elliott et al. ................. 514/521 |
| 5,055,491 A | * | 10/1991 | Yano et al. ................. 514/531 |
| 5,447,713 A | | 9/1995 | Elsner et al. |
| 5,657,574 A | * | 8/1997 | Kandathil et al. ............ 43/125 |

FOREIGN PATENT DOCUMENTS

| | | | |
|---|---|---|---|
| CN | 1173969 A | | 2/1998 |
| CN | 2356495 Y | | 1/2000 |
| CN | 2356495 | * | 11/2000 |
| GB | 2139498 A | | 11/1984 |

* cited by examiner

SUBSTANCE DELIVERY DEVICE

CROSS REFERENCE TO RELATED APPLICATIONS

This patent application claims priority under 35 U.S.C. § 365 from International Application Serial No. PCT/IB00/00883, filed Jun. 29, 2000, which claims priority from United Kingdom Application Serial No. 9915805.6, filed Jun. 29, 1999, which are herein incorporated by reference.

BACKGROUND OF THE INVENTION

The present invention relates to a substance delivery device comprising a paperboard strip, which includes at least one of substance toxic to insects or a perfume. The present invention also relates to a method for manufacturing such a device. More particularly, but not exclusively, the present invention relates to a mosquito coil comprising a paperboard coil impregnated with a substance toxic to mosquitoes and a method of manufacturing the same.

U.S. Pat. No. 5,447,713 discloses a mosquito coil manufactured from wood fibres and/or wood chips and a binder. The mixture of ingredients is pressed to form a board from which the coils are punched. The wood fibres or chips remain discrete and separate and are held together by the binder. The use of a binder to give the coil mechanical stability means that the coil tends to be brittle. A significant proportion of coils manufactured from such resin-bound boards are damaged either during distribution or by subsequent handling by the consumer.

SUMMARY OF THE INVENTION

In a first aspect, the pre nt invention provides a substance delivery device comprising a combustible paperboard strip and at least one of a substance toxic to insects and a perfume.

The term paperboard refers to fibrous structures which are made by felting fibres from a fluid suspension. The felting process results in the fibres becoming enmeshed with each other so providing a continuous matrix. The presence of enmeshed fibres such as result from a felting process can be detected by visual inspection of the product, optionally using magnifying apparatus such as a microscope. The resulting paperboard is more flexible (and so less brittle) than known resin-bound boards. A delivery device manufactured from such a paperboard is less likely to be damaged during packing, transit or subsequent handling than devices made by processes involving compression of fibres with a resin binder.

Known resin-bound delivery devices also tend to "dust" in that small particles tend to break from the coil during handling. This leaves a fine powder on the hands of the user and on any other surfaces with which the coil has been in contact. A significant mass of the coil can also be lost during transit through dusting leading to a reduction in the performance of the coil. The delivery device of the invention has the advantage that it has a reduced tendency to form "dust".

The delivery device of the invention can also be significantly lighter than known devices in which cellulose fibres are bound together by a resin, while still burning for the same amount of time. This can reduce distribution costs.

The use of a paperboard material in the delivery device of the invention means that the device can be produced in a wide range of colours by selection of a material on which images can be formed, for example using inks, for example by printing or other techniques. Known devices made from materials other than paperboard tend only to be produced in a limited range of colours, typically green or black, in some cases because of difficulties associated with printing on resin materials.

Preferably, the fibres comprise materials which are known for use in paper making, especially cellulosic fibres, more preferably waste paper fibres, especially kraft pulp. The papermaking fibre can be primary or secondary papermaking fibre. This makes the resulting delivery device relatively inexpensive to produce.

The fibres can comprise wood free fibres, preferably at least one of bagasse, straw or bamboo. This improves the flexibility of the resulting paperboard strip.

The fibres that are used to form the paperboard need to be long enough that they can mesh together to form a mechanically stable structure in which the fibres are largely retained without the use of an additional binder such as a resin material. The characteristics of suitable fibres which can form such a stable structure are known within the paper industry. Preferably, the length of the fibres that are used in the device of the present invention is at least about 0.1 mm, more preferably at least about 0.3 mm, especially at least about 1.0 mm. The length of the fibres can be greater than this for some applications, for example up to about 6.0 mm.

The fluid from which the fibres are felted can be aqueous based; water is particularly preferred.

Preferably, the strip is in the form of a coil. The coil will usually be helical so that the strip burns along a helical path. A strip can be formed with a helical configuration by stamping from a sheet.

The delivery device can include a flexible backing sheet for supporting the combustible paperboard strip. For a large range of strip widths, lengths and thicknesses, the paperboard strip might not be self supporting. Inclusion of such a backing sheet allows strips which are not self supporting, but which otherwise have satisfactory physical and burn characteristics, to be used. It also enhances the mechanical stability of the device.

The material of the flexible backing sheet can be selected so that it is not capable of self sustaining combustion. This prevents the backing sheet from burning faster than the paperboard strip. Preferred materials are paper-based, optionally treated with a flame retardant agent. Suitable flame retardant agents are known. However, it has been found surprisingly that little or no flame retardant agent need be applied to a paper-based backing sheet, to prevent it from burning faster than the paperboard strip, if the flammability of the paperboard strip is controlled appropriately, for example by control of the density of the strip and by use of combustion promotors and flame inhibitors.

The paperboard strip can include one or more combustion promoters. The promoter can be inherently combustible material, especially an organic material, for example a charcoal powder. The promoter might promote combustion in other ways, such as for example in the case of an oxidizing agent which can release of oxygen. An example of such an oxidizing agent is potassium nitrate. The charcoal powder or other combustion promoter is preferably present in the paperboard in an amount from about 0.25 to 10% by weight of the dry paperboard strip, more preferably from 0.5 to about 5%, for example from about 1 to about 2%.

The paperboard strip can include a dye, preferably an organic dye. The dye can function as a combustion promoter as well as affecting the visual appearance of the strip. The dye can preferably comprise 0.01% to 10% more preferably 0.5% to 2% by weight of the dry paperboard strip. Addition of the dye makes the combustion of the paperboard strip resistant to being extinguished by external factors such as a breeze. It also makes combustion insensitive to variations in internal properties of the paperboard strip.

The dye or other combustion promoter should preferably be distributed uniformly throughout the volume of the paperboard strip. The distribution of the dye has an impact on the combustion properties of the paperboard.

The paperboard can include one or more flame inhibitor agents. These will generally be particulate materials which are inherently non-combustible at temperatures encountered when the device of the invention is in use. Examples of suitable inhibitor agents include particulate inorganic materials such as calcium carbonate. The flame inhibiting properties of the agent can be affected by the size of the particles. In many cases, smaller particles will enhance the flame inhibiting effect. Preferably, at least 90% of the particles pass through a 150 μm aperture size mesh, more preferably through a 100 μm mesh, especially a 75 μm mesh.

The quantity of the flame inhibitor agent that is incorporated into the paperboard will depend on issues such as its particle size, the density of the board, the desired burn rate, and the presence and effect of any combustion promotors. Preferably, the flame inhibitor agent is present in an amount of at least about 1% by weight based on the weight of the dry fibre in the board, more preferably at least about 3%, for example about 5%. The amount of the flame inhibitor agent will generally be less than about 30% by weight based on the weight of the dry fibre in the board.

The paperboard strip can have a substantially rectangular cross section, the thickness of the strip preferably being in the range 0.2 to 1.9 mm, more preferably in the range 0.6 to 1.8 mm, the width of the strip preferably being in the range 2 to 6 mm, more preferably in the range 5 to 6 mm. Such paperboard strips can exhibit a substantially uniform burn rate and are not prone to self extinguish.

Preferably the density of the paperboard strip is at least 400 $kg.m^{-3}$, more preferably at least 550 $kg.m^{-3}$. Preferably its density is not more than 1000 $kg.m^{-3}$, more preferably not more than 850 $kg.m^{-3}$, especially not more than 750 $kg.m^{-3}$, for example not more than 650 $kg.m^{-3}$. The density can be controlled during the manufacture of the paperboard, for example by processes such as calendering.

Properties that are affected by the density of the paperboard include overall weight, burn rate, flexibility and mechanical stability of the structure. A relatively high density can be preferred for many applications because of the mechanical stability of the structure which allows it to be flexed without losing fibrous material. A high density also results in a reduced burn rate. However, the density should not be increased to such an extent that a flame tends to self-extinguish, for example when exposed to a draught.

In a further aspect of the invention there is provided a method of manufacture of a substance delivery device comprising the steps of:
  adding a furnish comprising fibrous structures to a fluid to form a fluid suspension;
  felting the fibrous structures from the fluid suspension to form a structure which comprises a mesh of interlocked fibres;
  drying the mesh to form a paperboard; and
  adding at least one of a substance toxic to insects or a perfume to the paperboard.

The resulting delivery device is flexible and so is less likely to be damaged than known devices either during transit or whilst being handled by the consumer. The invention includes substance delivery devices made by the method.

The method of the invention should preferably result in a device with a relatively low density, and the pressure that is applied to the fibres during the method, and the other conditions during manufacture of the device, should be selected accordingly. Generally, the method will include a step of calendering the fibres to reduce the thickness of the device. Preferably, the density of the finished device, after it has been dried, is not more than 1000 $kg.m^{-3}$, more preferably not more than 850 $kg.m^{-3}$, especially not more than 750 $kg.m^{-3}$, for example not more than 650 $kg.m^{-3}$.

Preferably the method includes a step of cutting the paperboard to form a strip, more preferably a coil, especially a helical coil.

Preferably, the method includes a step of attaching the paperboard to a flexible backing sheet, especially by means of an adhesive. The step of fastening the paperboard to the backing sheet should preferably take place after the mesh of interlocked fibrous structures has been formed, more preferably after the mesh has been at least partially dried to form a paperboard. The method can also include a step of drying the adhesive whilst restraining the paperboard and backing sheet to prevent distortion of the paperboard.

The furnish can comprise waste paper, preferably at least one of kraft pulp or newspaper waste. This makes the resulting delivery device relatively inexpensive to produce. It can also reduces the weight of the device.

The furnish can comprise wood free fibres, preferably at least one of bagasse, straw or bamboo. The use of wood free fibres rather than wood pulp is environmentally friendly.

The method can include a step of adding at least one of charcoal powder or a dye preferably an organic dye, to the fluid suspension. Preferably the dye is saturated or impregnated into the paper board. This improves the combustion properties of the resulting coil.

The method can include the step of adding a dye to the paperboard, preferably by saturation.

BRIEF DESCRIPTION OF THE DRAWINGS

The present invention will now be described by way of example only, with reference to the accompanying drawings in which:

FIGS. 2(*a*) to 2(*d*) show further embodiments of mosquito coils according to the invention in plan view;

DETAILED DESCRIPTION OF THE PREFERRED EMBODIMENTS

Figure 1:
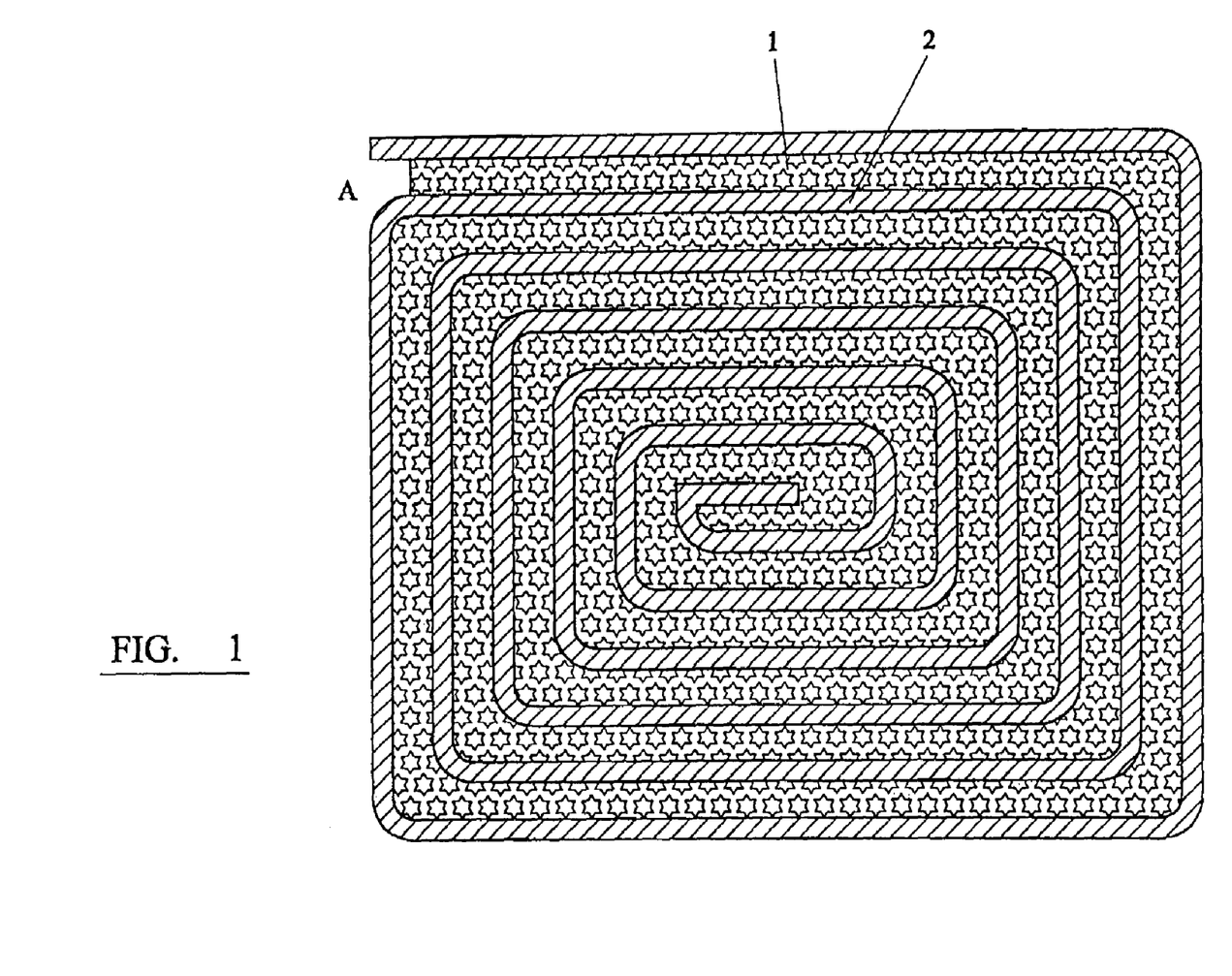
FIG. 1 shows a mosquito coil according to the invention in plan view.

FIG. 1 shows a mosquito coil according to the invention. The mosquito coil comprises a backing sheet 1 and a paperboard coil 2. The backing sheet 1 is a flexible paper sheet. The role of the backing sheet 1 is threefold: firstly, it provides reinforcement for the paperboard coil 2 so producing a dimensionally stable, flat, easy to handle coil; secondly, it enhances the performance of the coil by cutting off the air supply to one side of the paperboard coil 2 from one side. This can reduce the burn rate of the paperboard coil 2 by as much as 20%; thirdly, it serves as a medium for branding or other product information to be carried on the product.

The paper backing sheet 1 can be treated with a flame retardant additive to make it incapable of self sustaining combustion. Such an additive can be applied as a liquid by spraying. When the paperboard coil 2 is lit then the portion of the backing sheet 1 proximate to the burning end of the paperboard coil 2 can burn. However, because the backing sheet 1 cannot itself sustain combustion, combustion of the backing sheet 1 will not spread to areas of the backing sheet remote from the burning end of the paperboard coil 2. The combustion of the backing sheet 1 will therefore closely follow the paperboard coil 2, and it will not track across the backing sheet 1 away from the paperboard coil 2. It can therefore burn at the same rate as the paperboard coil 2.

The paper backing sheet 1 is manufactured from newsprint stock. This has the advantage that it can be coloured easily, for example using inks by printing techniques. It also combines a good rigidity with low weight characteristics. The low weight of the backing sheet 1 significantly reduces the cost associated with distribution of the mosquito coil. The unit weight of the paper backing sheet 1 is chosen to lie within the range about 30 to 300 $g.m^{-2}$, for example about 55 $g.m^{-2}$.

In order to manufacture a paperboard coil, a furnish which consists mainly of waste paper is taken and slushed along with an unbleached kraft pulp and newspaper waste. Wastepaper containing predominantly wood free fibres is used, for example fibres from bagasse, straw or bamboo. Such fibres give the resulting paperboard an suitable strength and density. Wood free fibres are also relatively inexpensive. A typical composition of the furnish is shown in table 1.

TABLE I

| Furnish | Dry weight (%) |
|---|---|
| Waste paper (high % of wood free fibre) | 75 |
| Unbleached wood pulp | 10 |
| Newsprint waste | 15 |

The slushing is done in water at a consistency of 2.5% in a hydropulper, according to established techniques used in the papermaking industry. After disintegrating the furnish so that an evenly mixed slurry of the fibre is obtained, an inorganic filler (for example calcium carbonate) is added and dispersed evenly by known methods. Immediately after this the pH of the mixture is raised to between 7 and 8 by, for example, the addition of sodium aluminate.

The slurry is then passed through a mild refining process well known in the papermaking art which results in a well dispersed fibre. After refining a solution of a cationic retention aid, (for example Sursolan™ K12L of BASF) is added which has the effect of fixing the inorganic filler to the fibre.

Optionally an organic dye can be added to the slurry, or preferably impregnated into the paperboard to enhance both the colour and burning characteristics of the final paperboard. Paperboards having an organic dye concentration in the region of 0.01 to 10% of the weight of the paperboard are to be preferred as this makes the combustion of the paperboard far more resistant to being extinguished by external factors such as a breeze. It also makes combustion more insensitive to internal properties of the paperboard.

Optionally, a charcoal powder can be added to the slurry during manufacture of the paperboard, to function as a combustion promoter, for example in an amount of about 2 to 5% by weight of the dry paperboard.

The slurry is then diluted to about 0.6% consistency and pumped to the headbox of a papermaking machine. The fibres are then felted from solution to form a mesh. The mesh is finally dried on conventional papermaking cylinders to form paperboard and sheeted at the end of the process.

By known papermaking techniques the density of the paperboard produced by the paper making machine is controlled to a target density of 0.55 $g.cm^{-3}$ and a thickness of 1.5 mm. Other thicknesses and densities are possible as discussed below.

A coil of the desired shape is then punched from the paperboard sheet and coated with an insect repellant. Coating can be done by known coating or printing techniques. One example of such a technique is to spray the coil with insect repellant and then allow it to dry. The resulting coil has an ash content of $3.4 \times 10^{-5}$ $kg.m^{-1}$ (0.00034 $g.cm^{-1}$) and a burn rate of approximately $6.6 \times 10^{-5}$ $m.s^{-1}$ (0.4 $cm.min^{-1}$). Examples of suitable insect repellant materials include pyrethroid insecticides such as pyrethrum, resmethrin, bioallethrin, allethrin and mixtures thereof; specific examples include pynamin forte, esbiothrin and natural pyrethrin. Other examples of insect repellant materials include citronella, lemon grass oil, lavender oil, cinnamon oil, clove oil, sandalwood oil and the insect growth regulator hydroprene. Perfumes can also be incorporated into the paperboard, for example with the insect repellant.

The paperboard coil 2 is adhered to the backing sheet 1 by an aqueous adhesive such as a starch or dextrin adhesive, typically with a solids content in the range 5% to 10%. The drying of the adhesive will cause the backing sheet 1 to shrink and the paperboard coil 2 to distort. To prevent this the paperboard coil 2 and backing sheet 1 are held under pressure between two plates in the form of a moving conveyor and the bottom plate is heated slightly to dry out the adhesive. Other types of adhesive can be used.

The paperboard coil 2 shown in FIG. 1 has a total length of 1.8 m, a strip width of 5 mm and a burn rate of $6.6 \times 10^{-5}$ $m.s^{-1}$ (0.4 $cm.min^{-1}$). The coil will therefore burn for about 7.5 hours.

Figure 2A:
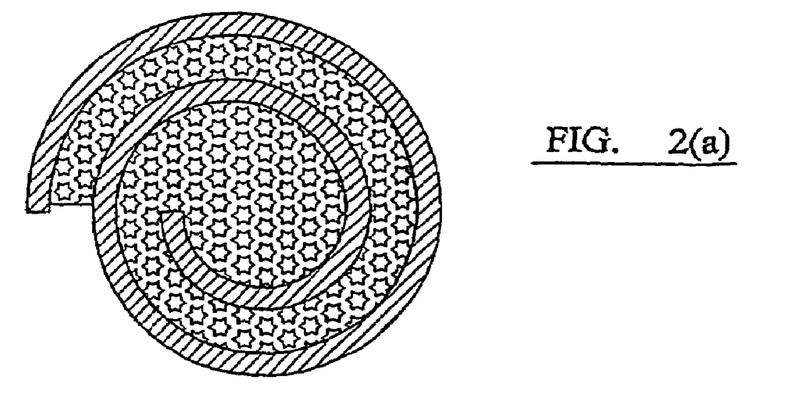
Figures 2B, 2C:
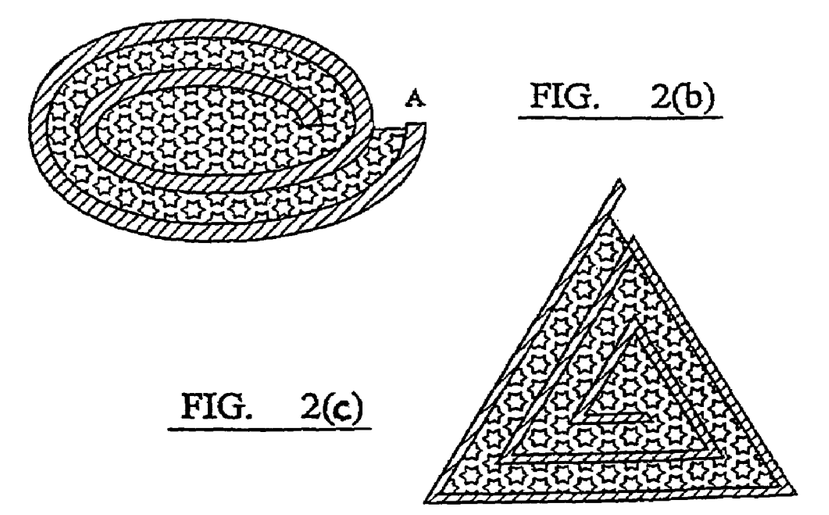
Figure 2D:
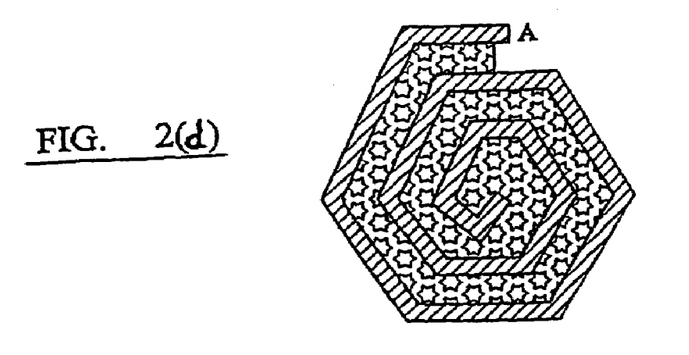

Shown in FIGS. 2(*a*) to 2(*d*) are a number of other embodiments of mosquito coils according to the invention.

The paperboard coil 2 of the mosquito coil shown in FIG. 1 has a rectangular cross section. The width, thickness and density of the paperboard coil 2 greatly influence the burn rate.

Figure 3:
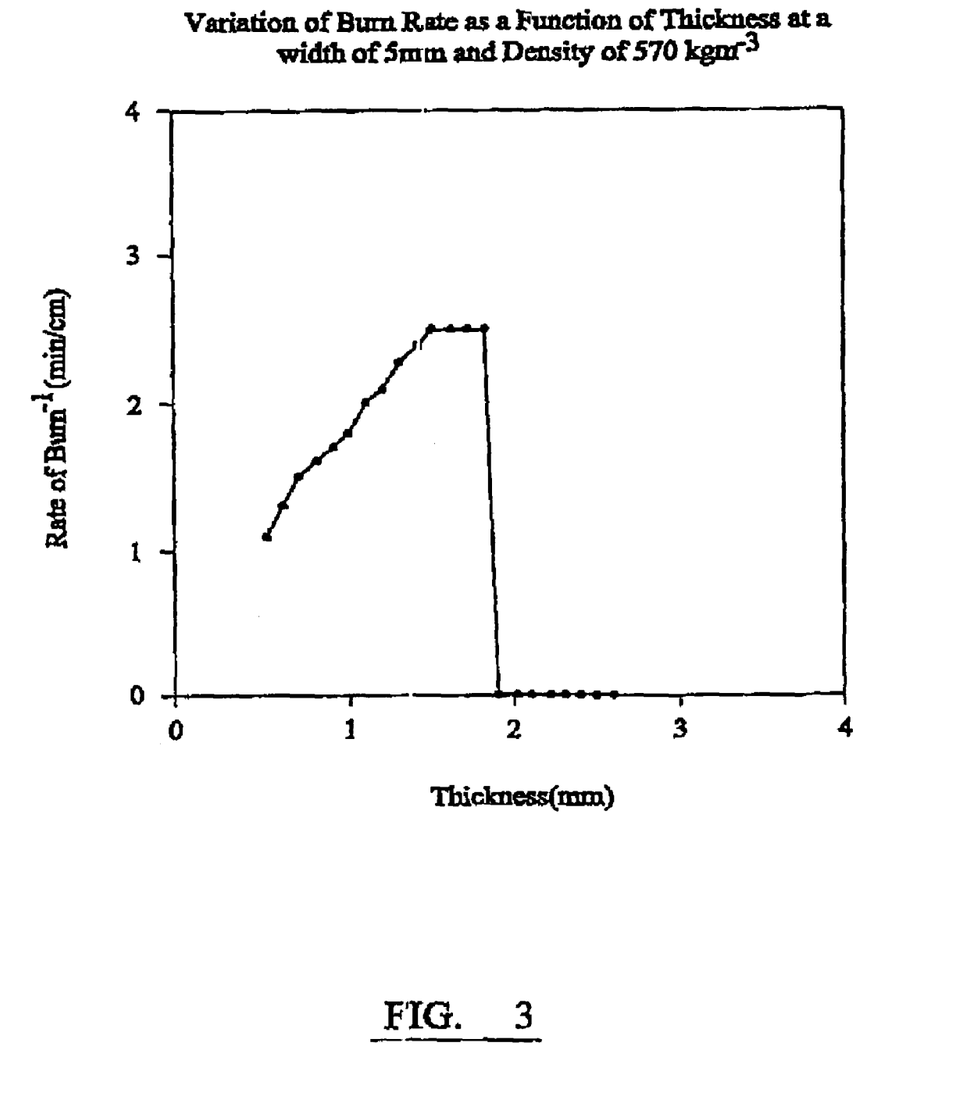
FIG. 3 illustrates the variation in burn rate with thickness for a rectangular paperboard strip of a mosquito coil according to the invention.

Shown in FIG. 3 is a graph of (burn rate)$^{-1}$ vs paperboard coil thickness at a constant coil width of 5 mm and a density of 570 $kg.m^{-3}$ (0.57 $g.cm^{-3}$). As the thickness of the paperboard coil is increased towards 1.8 mm, the (burn rate)$^{-1}$ increases from 6000 $s.m^{-1}$ to 15000 $s.m^{-1}$ (1 min/cm to 2.5 min/cm). At thicknesses larger than this the burn performance becomes uncertain with a marked tendency for the flame to extinguish itself. Mosquito coils of the invention have paperboard coils 2 having an optimum thickness of 1.5 mm, although paperboard coils 2 having thicknesses in the range 0.2 to 1.9 mm (more preferably in the range 0.6 to 1.8 mm) perform well.

Figure 4:
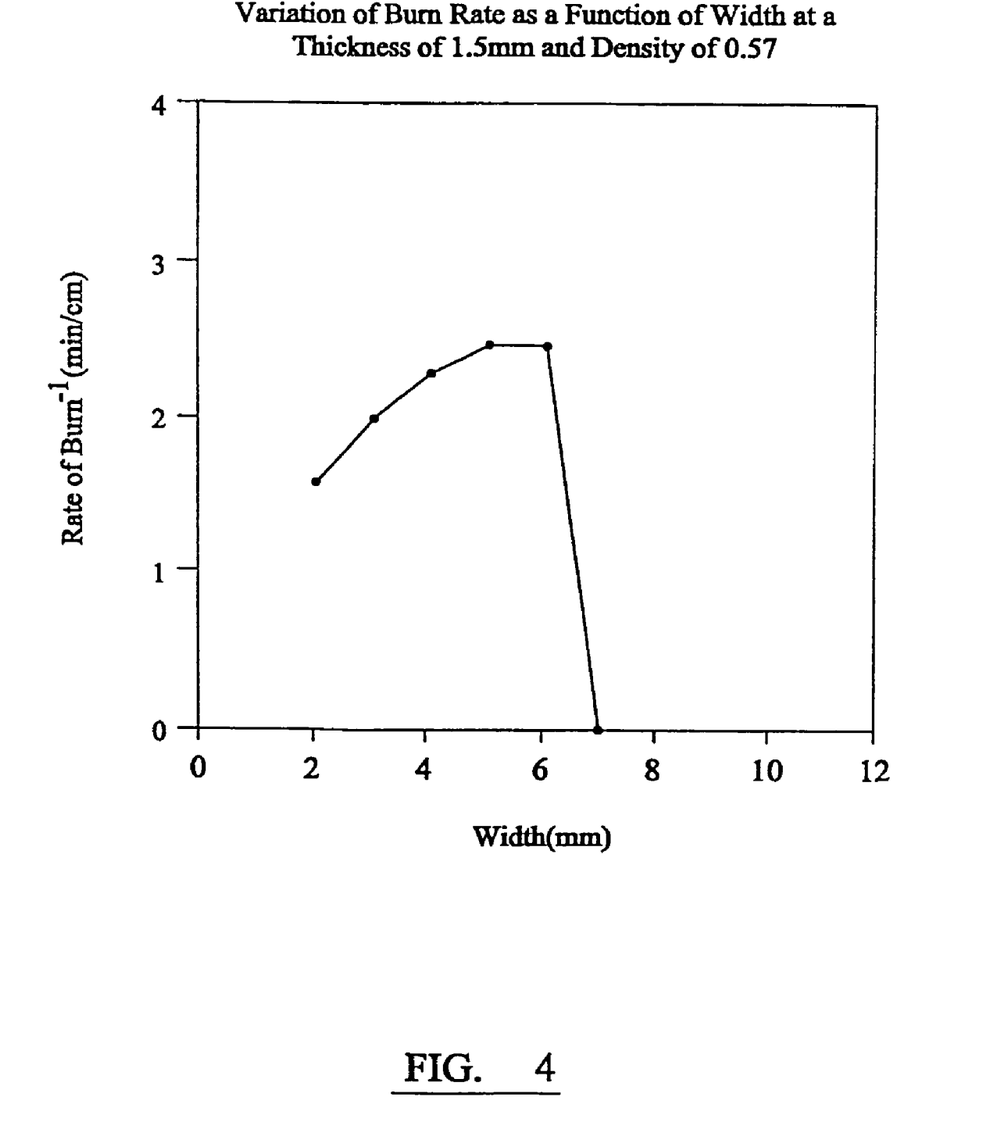
FIG. 4 illustrates the variation in burn rate with width for a rectangular paperboard strip of a mosquito coil according to the invention.

Shown in FIG. 4 is a graph of (burn rate)$^{-1}$ vs paperboard coil width at a constant thickness of 1.5 mm and a density of 570 $kg.m^{-3}$ (0.57 $g.cm^{-3}$). As can be seen, the burn rate drops as the coil widens, with the optimum width being reached at 5 to 6 mm. Thereafter the burn rate becomes uncertain with a marked tendency of the flame to extinguish itself. Coil widths in the range 2 to 6 mm (more preferably in the range 5 to 6 mm) perform well.

Figure 5:
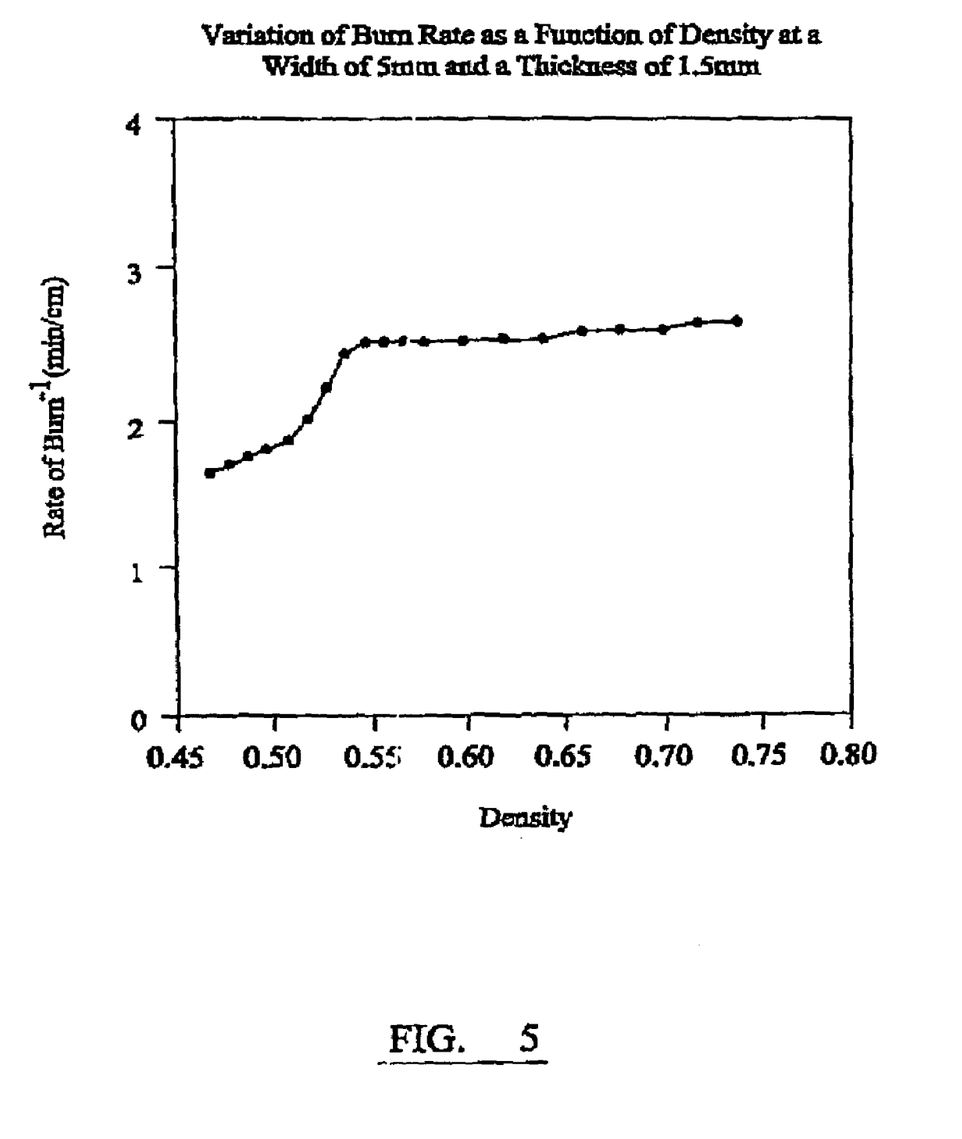
FIG. 5 shows the variation in burn rate with density for a paperboard strip of a mosquito coil according to the invention.

Shown in FIG. 5 is a graph of the inverted burn rate (burn rate$^{-1}$) vs paperboard coil density. As the density increases the porosity of the board is reduced causing the burn rate to lessen to the point of the flame being extinguished. As shown in FIG. 4 the burn rate slows down with increasing density until it is optimised at a density of approximately 550 kg.m$^{-3}$ (0.55 g.cm$^{-3}$). Thereafter the increase in paperboard density has only a very small to negligible impact on the burn rate up to a density of 740 kg.m$^{-3}$ (0.74 g.cm$^{-3}$). Paperboard coils according to the invention typically have densities in the range 400 to 700 kg.m$^{-3}$ (0.4 to 0.75 g.cm$^{-3}$). Densities in the range 550 to 650 kg.m$^{-3}$ (0.55 to 0.65 g.cm$^{-3}$) are to be preferred.

Whilst the above description reference has only been made to a device including an insect repellant, it is to be understood that the insect repellant can be replaced by or included together with a perfume.

The invention claimed is:

1. A substance delivery device comprising a combustible paperboard strip and at least one of a substance toxic to insects and a perfume, wherein said paperboard strip is formed from felting fibres from solution, wherein the density of said paperboard strip is not more than about 1000 kg.m$^{-3}$, the thickness of the strip being at least about 0.2 mm and not more than about 6 mm and said at least one substance can be delivered by combustion of said device.

2. A delivery device as claimed in claim 1, in which the strip is in the form of a coil.

3. A delivery device as claimed in claim 1 or claim 2, which includes a flexible backing sheet for supporting the combustible paperboard strip.

4. A delivery device as claimed in claim 3, in which the flexible backing sheet is not capable of self sustaining combustion.

5. A delivery device as claimed in claim 1, in which the material of the paperboard strip includes a combustion promoter.

6. A delivery device as claimed in claim 5, in which the combustion promoter is distributed substantially uniformly throughout the paperboard strip.

7. A delivery device as claimed in claim 1, in which the combustion promoter comprises a charcoal powder, the charcoal powder preferably being present in the paperboard at about 1 to 10% by weight of the dry paperboard.

8. A delivery device as claimed in claim 1, in which the paperboard strip has a substantially rectangular cross section, the thickness of the strip being at least about 0.2 mm and not more than about 1.9 mm.

9. A delivered device as claimed in claim 8, in which the width of the strip is at least about 2 mm and not being more than about 6 mm.

10. A delivery device as claimed in claim 1, in which the density of the paperboard strip is at least about 400 kg.m$^{-3}$.

11. A method of manufacture of a substance delivery device comprising the steps of adding a furnish comprising fibrous structures to a fluid to form a fluid suspension;
   felting the fibrous structures from the fluid suspension to form a mesh of interlocked fibrous structures;
   drying the mesh to form a paperboard; and,
   adding at least one of a substance toxic to insects or a perfume to the paperboard, and cutting the paperboard to form at least one strip,
   wherein the density of the paperboard strip is not more than about 1000 kg.m$^{-3}$, the thickness of the paperboard strip being at least about 0.2 mm and not more than about 6 mm, and at least one substance can be delivered by combustion of said strip.

12. A device as claimed in claim 1, wherein said substance toxic to insects is at least one substance selected from the group consisting of a pyrethroid insecticide, citronella, lemon grass oil, cinnamon oil, clove oil, sandalwood oil, and an insect growth regulator.

13. A method as claimed in claim 11, wherein said substance toxic to insects is at least one substance selected from the group consisting of a pyrethroid insecticide, citronella, lemongrass oil, cinnamon oil, clove oil, sandalwood oil, and an insect growth regulator.

14. A method as claimed in claim 11, which includes the step of attaching the paperboard to a flexible backing sheet.

15. A method as claimed in claim 14, in which the backing sheet is attached by means of an adhesive, and in which the method includes the step of drying the adhesive while restraining the paperboard and backing sheet to prevent distortion of the paperboard.

16. A method as claimed in claim 11, in which the furnish comprises waste paper.

17. A method as claimed in claim 11, in which the furnish comprises wood free fibers.

18. A method as claimed in claim 11, which further comprises the step of adding a combustion promoter to the fluid suspension.

19. A method as claimed in claim 18, wherein the combustion promoter comprises at least one of a charcoal and an organic dye.

20. An insect repellant device comprising a combustible paperboard strip which includes a substance toxic to insects, wherein said paperboard strip is formed from felting fibres from solution, wherein the density of said paperboard strip is not more than about 1000 kg.m$^{-3}$, the thickness of the strip being at least about 0.2 mm and not more than about 8 mm, said at least one substance toxic to insects can be delivered by combustion of said device, and said substance toxic to insects is at least one substance selected from the group consisting of a pyrethroid insecticide, citronella, lemon grass oil, cinnamon oil, clove oil, sandalwood oil, and an insect growth regulator.

21. A method of manufacture of an insect repellant device comprising the steps of:
   adding a finish comprising fibrous structures to a fluid to form a fluid suspension;
   felting the fibrous structures from the fluid suspension to form a structure which comprises a mesh of interlocked fibres;
   drying the mesh to form a paperboard;
   cutting the paperboard into at least one strip and,
   adding a substance toxic to insects to the paperboard, wherein the density of said paperboard strip is not more than about 1000 kg.m$^{-3}$ and said strip being of a density and thickness capable of maintaining combustion of itself after combustion is initiated, wherein said at least one substance toxic to insects can be delivered by combustion of said device and said substance toxic to insects is at least one substance selected from the group consisting of a pyrethroid insecticide, citronella, lemon grass oil, cinnamon oil, clove oil, sandalwood oil, and an insect growth regulator.

22. A delivery device as claimed in claim 5, in which the combustion promoter is comprised of an organic dye.

23. A method as claimed in claim 11 wherein the step of cutting the paperboard to form a strip forms a strip is in the form of a coil.

24. A method as claimed in claim 17 wherein the wood free fibers are comprised of straw.

25. A method as claimed in claim 17 wherein the wood free fibers are comprised of bamboo.

26. A delivery device as claimed in claim 1, in which the paperboard strip has a substantially rectangular cross section, the thickness of the strip being at least about 0.6 mm and not more than about 1.8 mm.

27. A delivery device as claimed in claim 1, in the which the width of the strip is at least about 5 mm and not more than about 6 mm.

28. A delivery device as claimed in claim 1, in which the density of the paperboard strip is at least, about 550 kg.m$^{-3}$ and not more than about 650 kg.m$^{-3}$.

29. A method as claimed in claim 16 wherein the waste paper is comprised of kraft pulp.

30. A method as claimed in claim 16 wherein the waste paper is comprised of newspaper waste.

31. A method as claimed in claim 17 wherein the wood free fibers are comprised of bagasse.

* * * * *